United States Patent
Schreiner et al.

(10) Patent No.: US 9,248,243 B2
(45) Date of Patent: Feb. 2, 2016

(54) LABEL FOR AFFIXING TO A SYRINGE BODY

(71) Applicant: SCHREINER GROUP Gmb H & Co. KG, Oberschleissheim (DE)

(72) Inventors: Helmut Schreiner, Munich (DE); Mark Walter, Unterschleissheim (DE); Robert Meukel, Gauting (DE); Winfried Langenkamp, Munich (DE)

(73) Assignee: SCHREINER GROUP Gmb H & Co. KG, Oberschleissheim (DE)

( * ) Notice: Subject to any disclaimer, the term of this patent is extended or adjusted under 35 U.S.C. 154(b) by 291 days.

(21) Appl. No.: 13/929,467

(22) Filed: Jun. 27, 2013

(65) Prior Publication Data

US 2014/0005608 A1 Jan. 2, 2014

(30) Foreign Application Priority Data

Jun. 28, 2012 (DE) .......... 10 2012 105 693

(51) Int. Cl.
| | |
|---|---|
| *A61M 5/32* | (2006.01) |
| *G09F 3/02* | (2006.01) |
| *G09F 3/10* | (2006.01) |
| *B32B 3/16* | (2006.01) |
| *B32B 3/26* | (2006.01) |
| *B32B 3/30* | (2006.01) |

(52) U.S. Cl.
CPC ........... *A61M 5/3202* (2013.01); *A61M 5/3216* (2013.01); *G09F 3/02* (2013.01); *G09F 3/10* (2013.01); *A61M 2005/3284* (2013.01); *B32B 3/16* (2013.01); *B32B 3/263* (2013.01); *B32B 3/30* (2013.01); *G09F 2003/0266* (2013.01); *G09F 2003/0272* (2013.01); *Y10T 29/5198* (2015.01)

(58) Field of Classification Search
CPC ........... A61M 2005/32844; A61M 2005/3212; A61M 5/3278; A61M 5/3202; A61M 5/321; A61M 5/3216; A61M 5/3213; G09F 3/02; G09F 3/10; G09F 3/0295; G09F 2003/0251; G09F 2003/0266; G09F 2003/0272; G09F 2013/189; Y10T 29/5198; B32B 3/16; B32B 3/263; B32B 3/30; B32B 37/02; B32B 37/025
See application file for complete search history.

(56) References Cited

U.S. PATENT DOCUMENTS 4,704,177 A * 11/1987 Vaillancourt ..... A61M 39/1011
128/DIG. 26
5,135,507 A * 8/1992 Haber ................... A61M 5/002
604/110

(Continued)

FOREIGN PATENT DOCUMENTS

| DE | 102006048209 A1 | 4/2008 |
|---|---|---|
| DE | 202008017330 U1 | 7/2009 |

(Continued)

*Primary Examiner* — Jason L Vaughan
(74) *Attorney, Agent, or Firm* — Studebaker & Brackett PC

(57) ABSTRACT

A method for producing a label for affixing to a syringe body, which label on both sides of an extension area comprises a first flat side and a second flat side,
  a first label region, which is wrappable about the syringe body,
  a second label region, which is joined to the first label region and which on the first flat side and/or the second flat side comprises a needle receiving device for a syringe needle for the protection from injuries through the syringe needle. The needle receiving device is produced into a receiving device region wholly or partly forming the needle receiving device by applying a build-up layer onto a carrier substrate of the second label region and moulding the build-up layer on the carrier substrate.

11 Claims, 10 Drawing Sheets

(56) References Cited

U.S. PATENT DOCUMENTS

Figure 1:
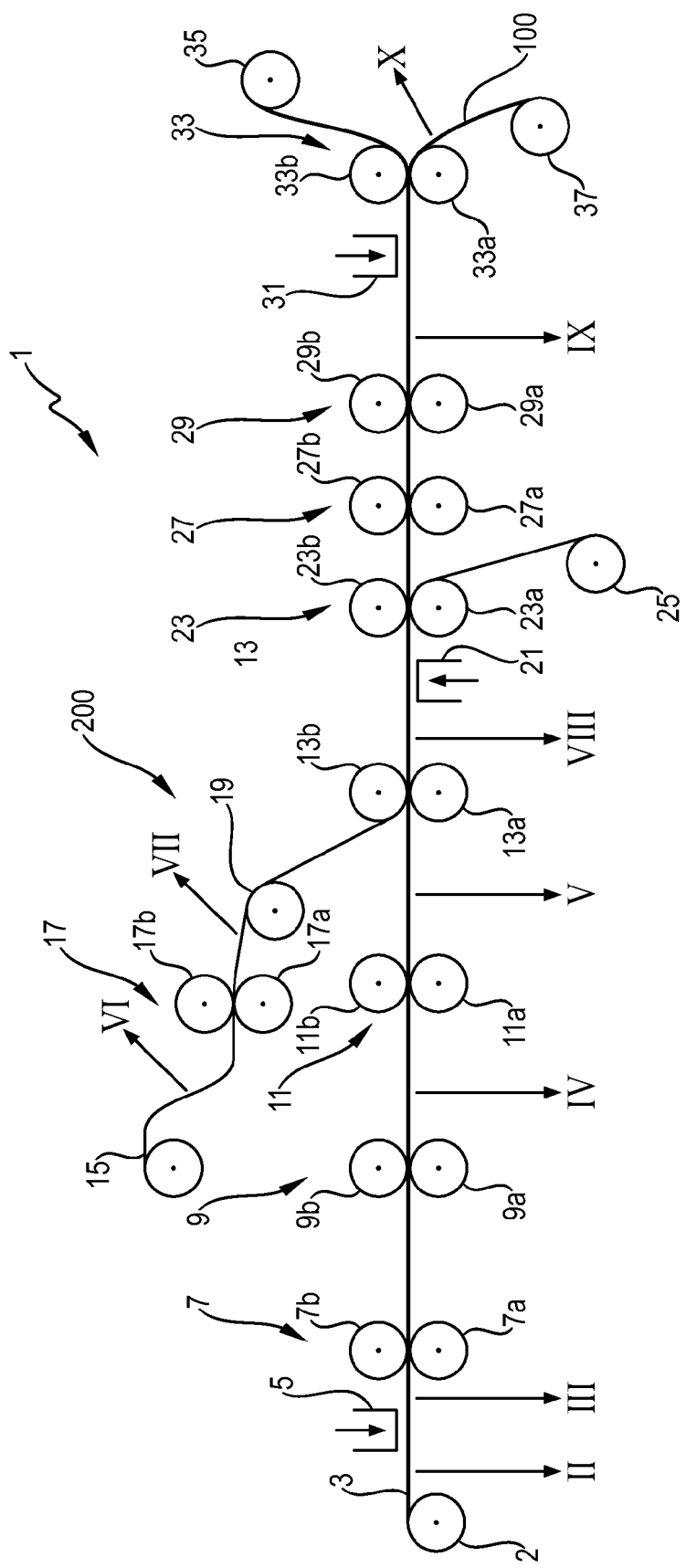
Figure 4A:
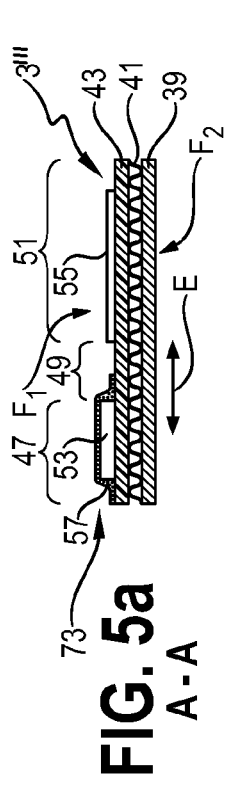
Figure 4B:
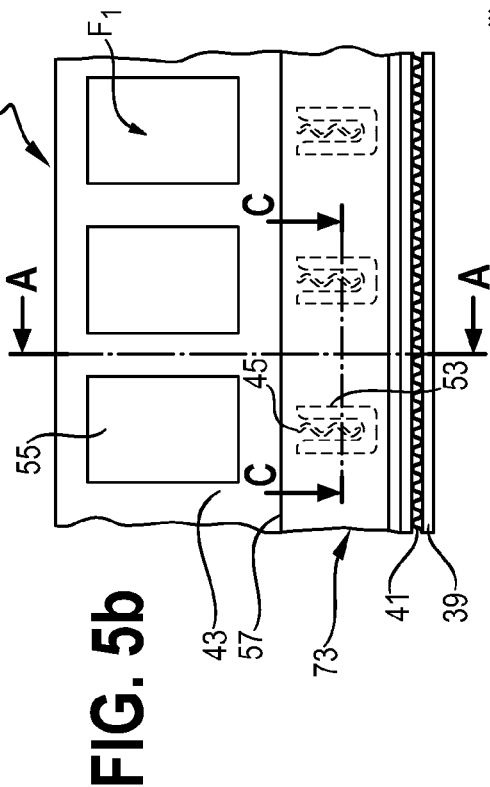
Figure 4C:
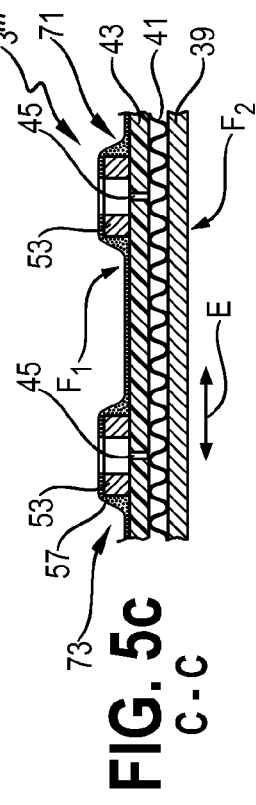

| | | | | |
|---|---|---|---|---|
| 6,328,713 | B1 * | 12/2001 | Hollister | A61M 5/3216 604/192 |
| 8,377,007 | B2 | 2/2013 | Moosheimer et al. | |
| 8,671,602 | B2 * | 3/2014 | Seidl | B62M 1/38 283/81 |
| 8,777,910 | B2 * | 7/2014 | Bauss | A61M 5/3216 604/192 |
| 2007/0176410 | A1 * | 8/2007 | Unglert | G09F 3/10 283/67 |
| 2009/0054847 | A1 | 2/2009 | Bauss et al. | |
| 2009/0291240 | A1 | 11/2009 | Moosheimer et al. | |

FOREIGN PATENT DOCUMENTS

| | | |
|---|---|---|
| EP | 1566786 A1 | 8/2005 |
| EP | 2302610 A2 | 3/2011 |
| WO | 2006/105807 A1 | 10/2006 |
| WO | 2008/046722 A1 | 4/2008 |

* cited by examiner

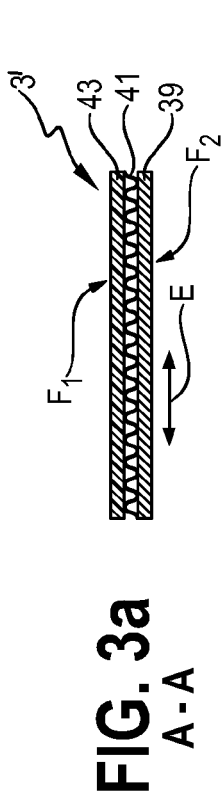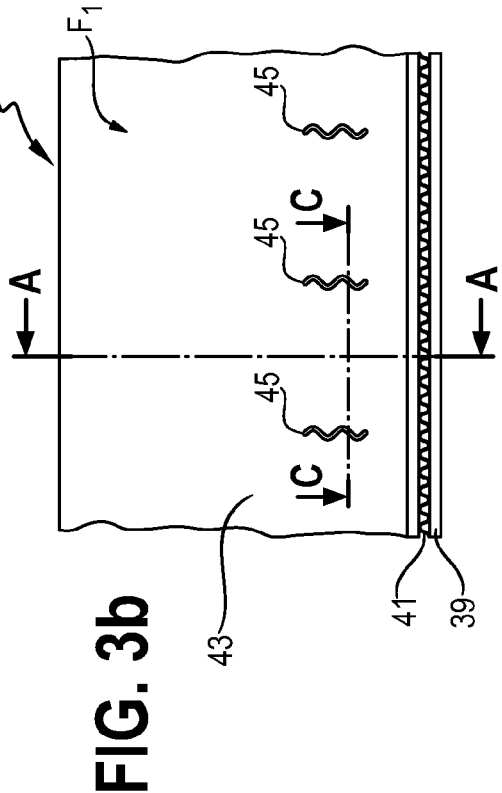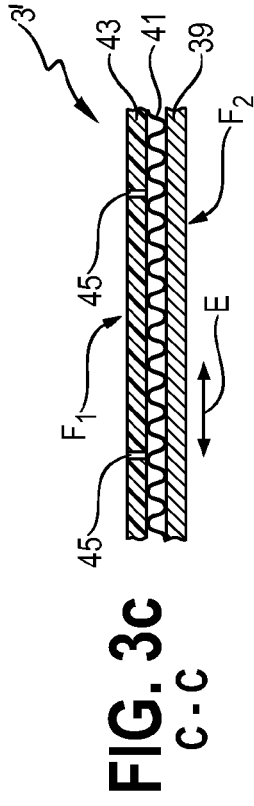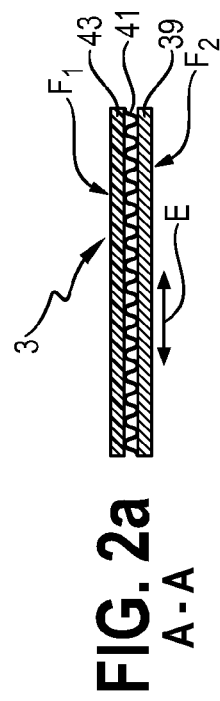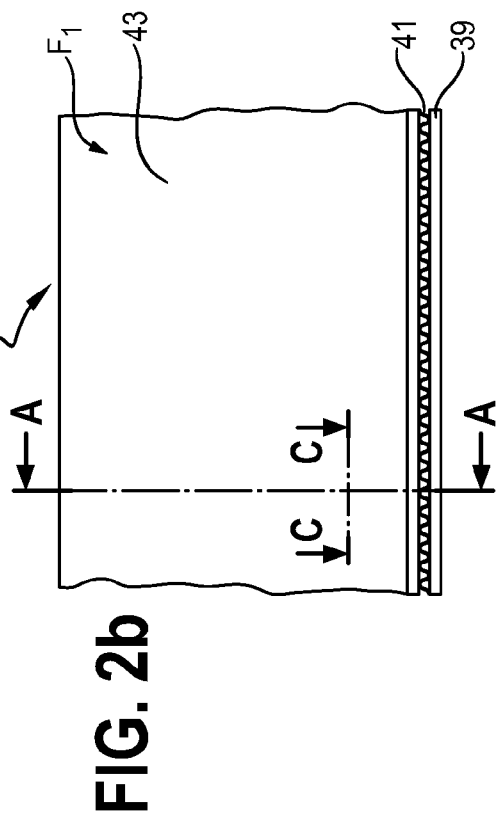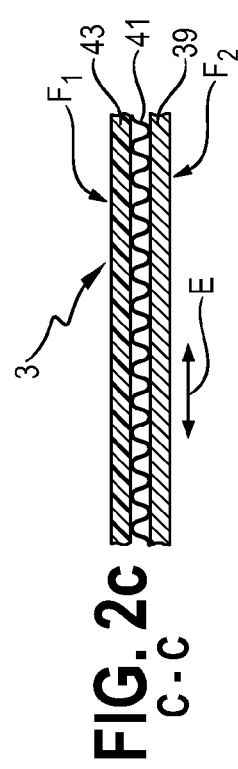

A-A

C-C

A-A

C-C

A-A

C-C

A-A

C-C

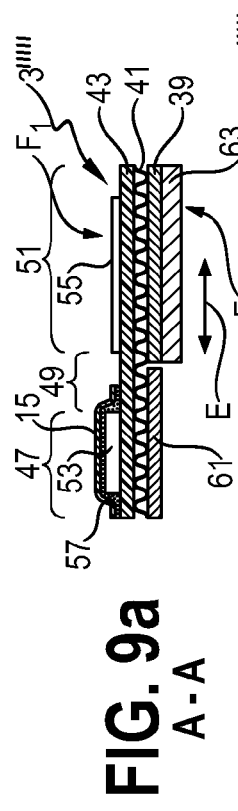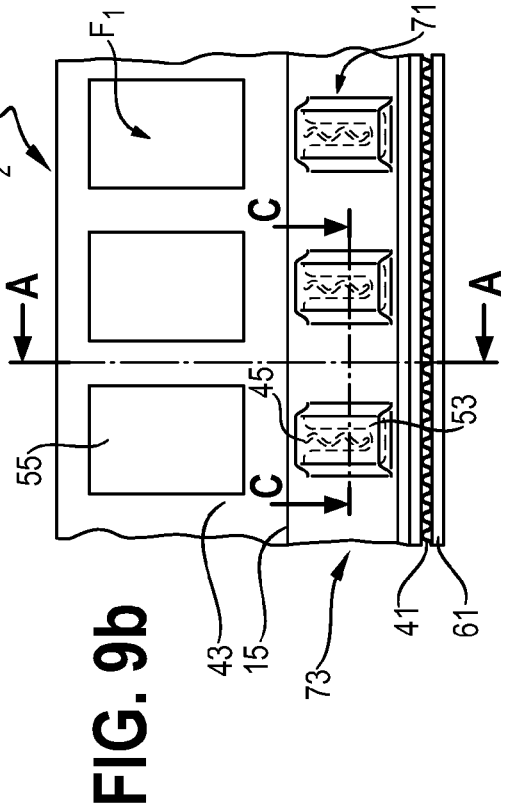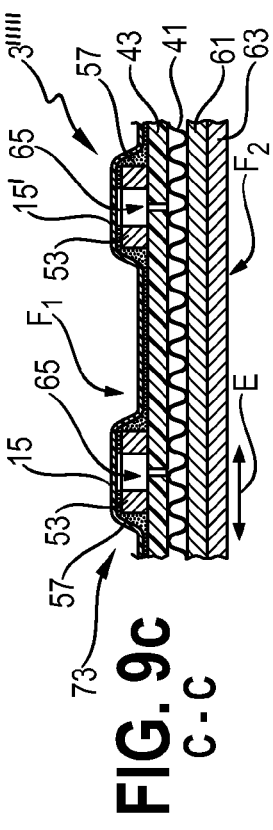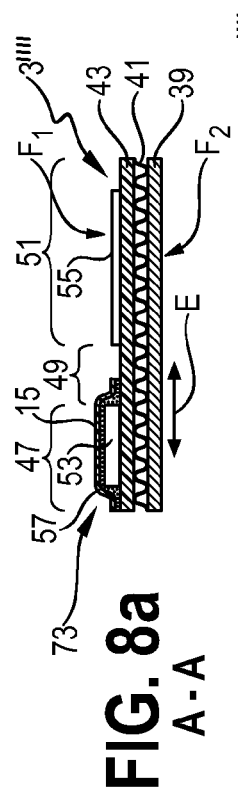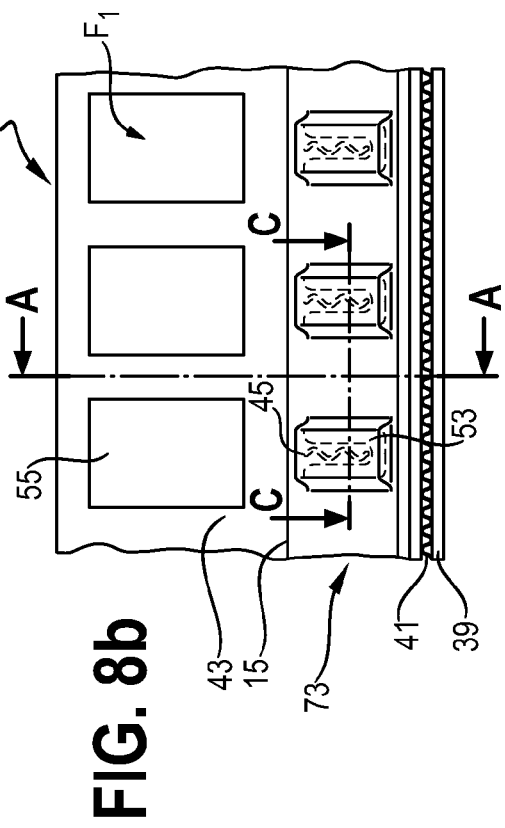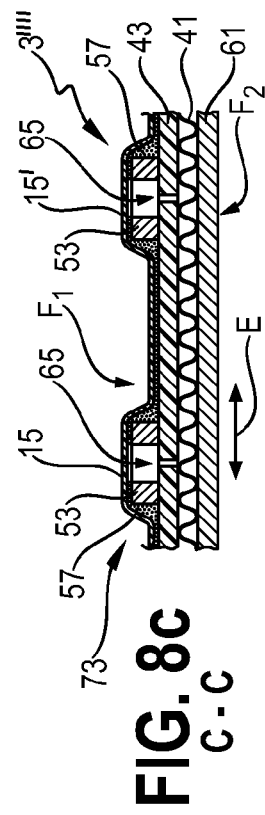
FIG. 8a A-A    FIG. 8b    FIG. 8c C-C
FIG. 9a A-A    FIG. 9b    FIG. 9c C-C

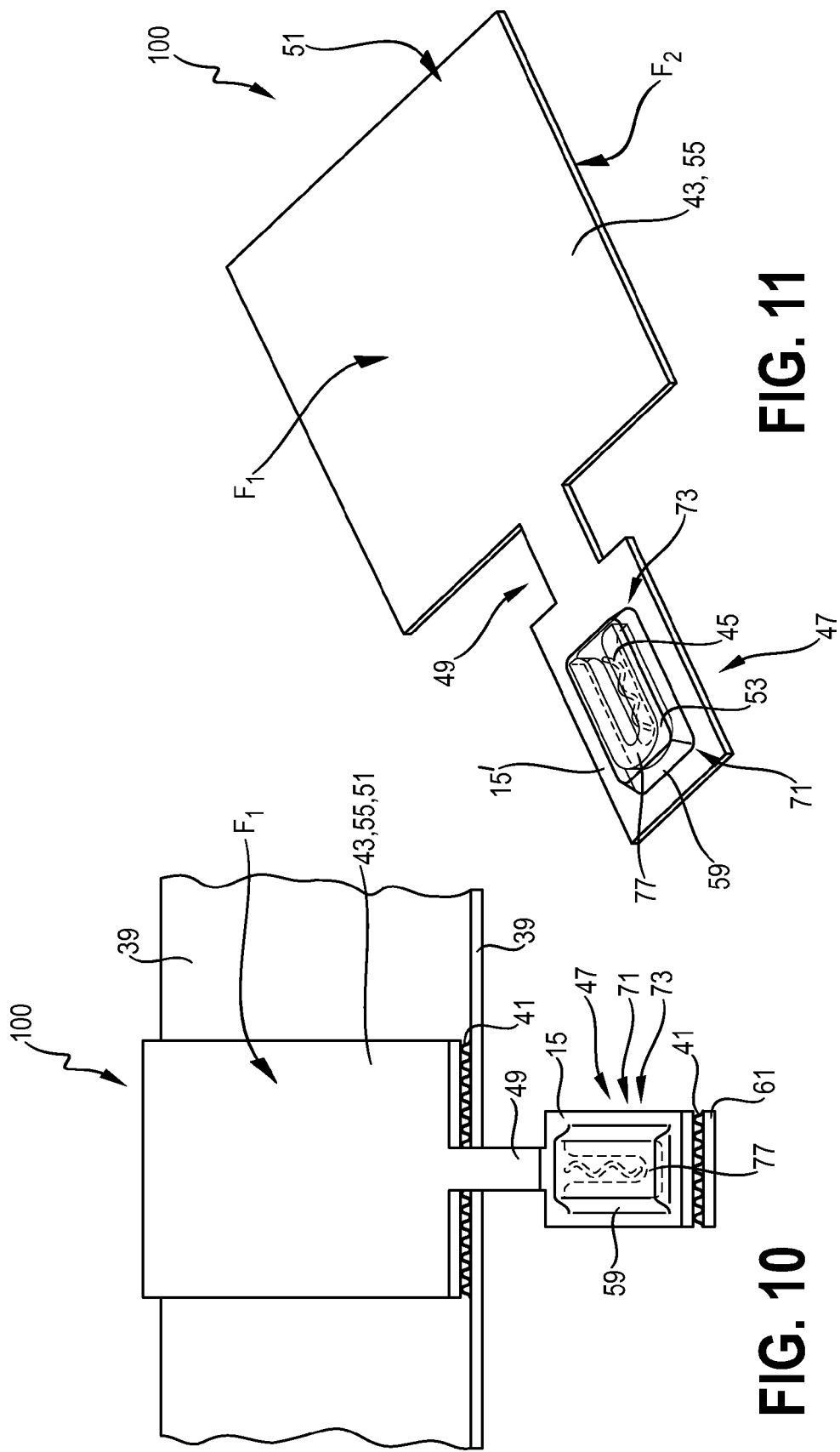

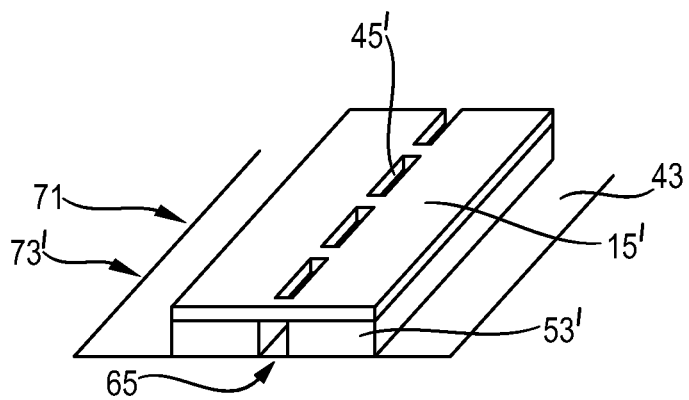
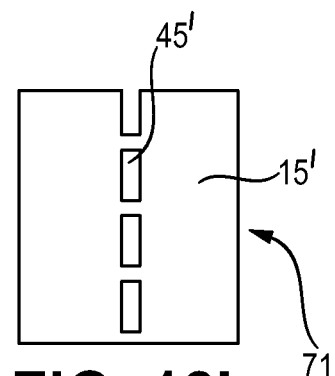
FIG. 12a   FIG. 12b
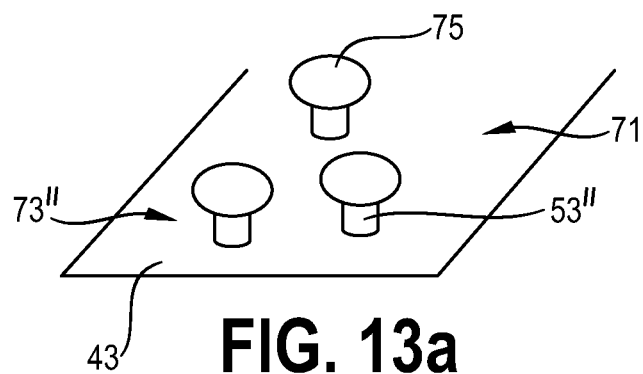
FIG. 13a
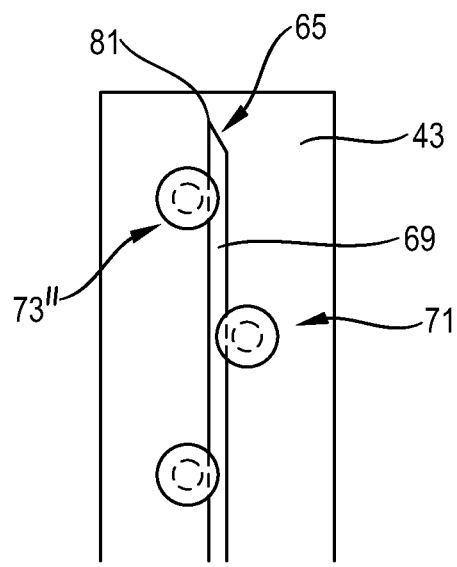
FIG. 13b

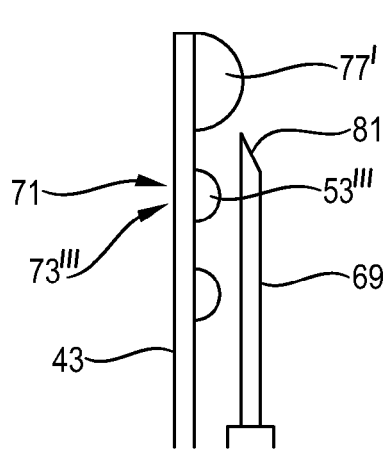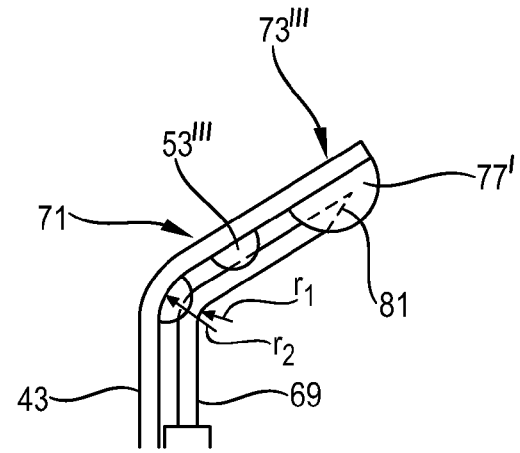
FIG. 14a    FIG. 14b
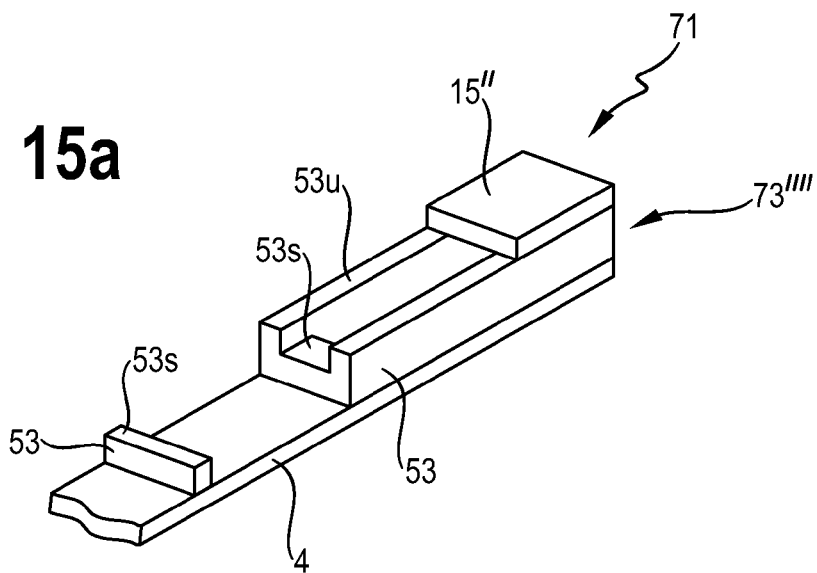
FIG. 15a
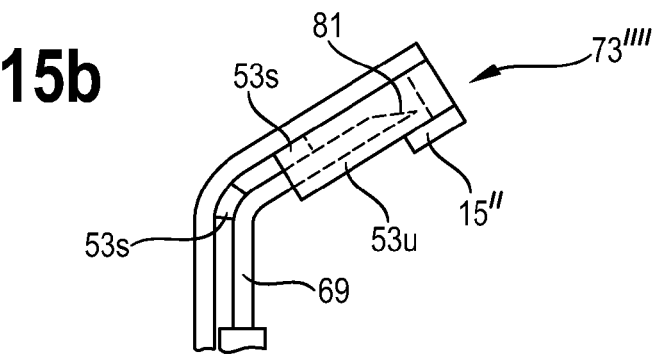
FIG. 15b

LABEL FOR AFFIXING TO A SYRINGE BODY

The present invention relates to a method for producing a label for affixing to a syringe body, which label comprises a first flat side and a second flat side and the following elements on both sides of an extension area:
- a first label region which is wrappable about the syringe body,
- a second label region, which is joined to the first label region and which, on the first flat side and/or the second flat side, comprises a needle receiving device for a syringe needle for the protection from injuries through the syringe needle.

The invention also relates to such a label, a syringe body with such a label and a machine for producing such a label.

The principle of labels with needle receiving devices is known from WO 2006/105807 A1. Special embodiments of such labels are described in more detail in DE 10 2006 048 209 A1, DE 20 2008 017 330 U1, EP 2 302 610 A2 and WO 2008/046722 A1. The disclosure content of these applications is considered as part of the disclosure of the application present here.

All such label products derived from the prior art substantially have in common that on the one hand they comprise a label as label part and on the other hand an affixed injection moulding as needle receiving device joined to the label part, i.e. two separate function parts which have to be elaborately joined through a pick-and-place process. For while the label part can be produced by means of conventional printing, laminating and punching operations thoroughly known in the labelling technology, the injection moulding has to be separately moulded in an injection mould and then subsequently joined to the label part. These processes are comparatively elaborate and cost-intensive.

An object of the present invention therefore consists in creating a label of the type mentioned at the outset which can be more easily produced but preferably has the same degree of safety from injuries as a label according to the prior art. The aim preferably is to largely avoid pick-and-place processes in particular.

This object is solved through a method according to claim 1.

Accordingly, the label according to the invention mentioned at the outset is further developed in that the needle receiving device is produced by applying a build-up layer on a carrier substrate of the second label region and moulding the build-up layer on the carrier substrate into a receiving device region wholly or partly forming the needle receiving device.

"Syringe body" at the outset and in the following is to describe a device which comprises a syringe needle or is formed as being capable of being joined to said needle to form a syringe. In particular, this is therefore to mean the body of a syringe (filled with a serum or unfilled) with integrated syringe needle, a readymade cannula for applying to a body of a syringe or a body of a syringe with applied cannula.

The extension area of the label is the area of the label which during the production in a state not applied to the syringe body is substantially flat as a rule. This area is usually curved later on when the label is attached to the syringe body, wherein the label can be applied about the syringe body also overlapping itself and if applicable also multiply overlapping itself, i.e. "over round about".

The first label region is therefore wrappable about the syringe body (wherein "wrappable" again is to mean that possibly the syringe body is only covered by the label along a part circumference), preferably also glued onto said syringe body. To this end, it can then be equipped on its flat side facing the syringe body at least over part of the area, preferably over the full area (in order to achieve a stronger adhesive effect) preferentially with a pressure-sensitive adhesive which is particularly preferably at least partially permanently adhering to the syringe body. Alternatively, the first label region can also be formed as a sleeve label, which is put over the syringe body and adapted to the latter—for example through shrinking methods. Such an adaptation is therefore defined as "wrapping" in the sense of "wrappable".

The first label region comprises at least one substrate which acts as a carrier, wherein (if applicable additionally to the adhesive) printing can be carried out on at least one of its flat sides, in particular an information printing regarding the content of the syringe body. This substrate can comprise paper and/or cardboard, but preferably a film, in particular preferably a plastic film. In order to ensure the wrappability of the first label region about the syringe body, the substrate has a suitably selected flexibility, i.e. in particular elasticity or pliability which can be adapted to the radius of the syringe body by selecting a substrate material suitable for this purpose and a corresponding substrate thickness. The second label region preferably, but not necessarily, comprises the same substrate as the first label region. This substrate or a further substrate of the second label region acts as a carrier substrate of the second label region.

On this label substrate, a build-up layer is applied according to the invention and subsequent to the application and/or at the same time as the application moulded on the carrier substrate. The build-up layer, which can also be described as receiving build-up layer, forms a receiving device region through this moulding, which wholly or at least partially forms the needle receiving device. In this connection it is pointed out that the term "moulding" of the build-up layer also includes a shaping of this build-up layer directly during its application, for example through suitably selective application, for example in the form of a selective printing or similar. To distinguish between the pure application of the build-up layer and the "moulding", the following criteria can be utilised in particular:

a) the build-up layer is higher in regions than its original height upon the application and/or
b) the build-up layer does not extend over the entire carrier substrate, but is applied only partially, i.e. in regions along the corresponding surface of the carrier substrate and/or
c) the height of the build-up layer exceeds a height of approximately 50 µm, i.e. the height of a usual screen printing layer, preferably a height of 100 µm, particularly preferably a height of 250 µm.

In all these three cases, this can be described as a "moulding" of the build-up layer, since the build-up layer is specifically subjected to an intentional shaping during and/or after the application. By contrast, the pure application for example full-area printing or coating with a layer is not a moulding in this sense.

By moulding the build-up layer on the carrier substrate, a substantial process step compared with the prior art, i.e. compared with pick-and-place processes can be saved: for the moulding can directly take place on a carrier substrate of the label and not specifically separately from the label production process in a separate injection moulding machine. Because of this it becomes possible to produce the entire label within the scope of the thoroughly known label production technologies, i.e. purely through the known processes of printing, stamping, hardening, coating, lining and laminating (the two last terms are used synonymously in the application for the sake of simplicity), punching, cutting, weeding and lasering. In particular, the entire label, and this is particularly preferred, can be produced in an integrated roll-to-roll process, which means that all starting products are either fed or coated from a roll and at the end a roll (or several) is present, on which the label as end product is bound.

The method according to the invention in particular helps in saving elaborate process steps such as for example the separate production of an injection moulding and the pick-and-place method and thus makes possible a significantly simpler production of a label mentioned at the outset. This can also save expenditure in setting up and/or maintaining the machines, just as material and ultimately product and production costs. At the same time, the invention has the potential of substantially reducing production waste and thus supplying an even more reliable product than previously.

According to the invention, a label of the type mentioned at the outset is suitably further developed in that the needle receiving device comprises a build-up layer on a carrier substrate of the second label region, which on the carrier substrate is moulded into a receiving device region wholly or partly forming the needle receiving device. Since the label is designed for attachment to a syringe body, the invention furthermore also comprises a syringe body having such a label according to the invention.

A machine of the type mentioned at the outset is further developed according to the invention in that it comprises an application and moulding device which are designed in order to produce during the operation the needle receiving device by applying a build-up layer to a carrier substrate of the second label region and moulding the build-up layer on the carrier substrate into a receiving device region wholly or partly forming the needle receiving device. Here, the application and moulding device can be realised as a single unit, preferably, however, it comprises a plurality of function modules or stations between which other modules or stations are also arranged. The function modules or stations can include in particular:

printing units,
cutting or punching units,
dryer or cross-linking units,
lining/laminating units,
coating units,
stamping units,
laser ablation stations,
deflection rollers,
wrapping units,
and much more.

These function modules or stations in their entirety then act together so that they fulfil the complete function of the application and moulding device.

Further particularly advantageous configurations and further developments of the invention are obtained from the dependent claims and the following description. Here, the label and the machine can also be further developed into the method according to the dependent claims and in each case vice versa.

Preferably, for creating the build-up layer, a plurality of part build-up layers is applied. This means that the part build-up layers acting together form the build-up layer, which because of this can be formed correspondingly more functional or geometrically complex. For example, a plurality of part build-up layers can increase an overall height of the build-up layer (measured from the carrier substrate) and/or more complex geometrical shapes of the build-up layers can be produced, for example using different extensions or extension directions parallel to the carrier substrate.

Here, at least two of the part build-up layers preferentially comprise different materials, for exactly by selecting different materials can an individual function be assigned to each of the part build-up layers. A first, for example lower, part build-up layer can for example serve for creating a first distance away from the carrier substrate, while a second part build-up layer on the first part build-up layer, which is further away from the carrier substrate can fulfil a clamping or engagement function for the syringe needle. Obviously, any other function combinations in addition to this highly advantageous combination previously mentioned are also conceivable.

A particularly preferred possibility when using a plurality of part build-up layers alternatively or additionally to the different material selection consists in that at least two part build-up layers are dimensioned differently in size in their respective extension planes substantially located parallel to the extension surface. Such a geometrical differentiation of different part build-up layers likewise makes possible assigning different functions to the part build-up layers in a simple and targeted manner. Here, a first part build-up layer, which is positioned closer to the carrier substrate than a second part build-up layer, is particularly preferably dimensioned smaller at least in regions in a direction along its extension plane than the second part build-up layer along its extension plane. Because of this, the second part build-up layer projects over the first part build-up layer cantilever-fashion at least in regions. For example, an (overall) build-up layer can be altogether realised which at least in a cross-sectional plane has a mushroom shape, wherein the first part build-up layer forms the stem shape of the mushroom shape and the second part build-up layer projecting over the first part build-up layer cantilever-fashion, an associated hat shape. Other forms can also be realised, such in which the second part build-up layer projects cantilever-fashion the first only in one space direction and/or only in one part region. Particularly preferably, the second build-up layer comprises a film-like upper layer, which is at least in regions arranged substantially parallel to the extension surface.

As film or general substrate, such an upper layer can be laminated onto the first build-up layer or the latter lined with the former. This is particularly desirable when the film-like upper layer is to be designed particularly sturdily, in particular particularly tear-resistant and/or particularly load-bearing. The film-like upper layer however can also be printed and then extend over a region or part region of the first part build-up layer like a film-like covering. An application by printing is appropriate when the upper film only has to exercise a minor holding or bridging function over regions of the first part build-up layer, for the print application is less material and process-intensive and therefore more easily integratable in the usual manufacturing process of labels. With preferred variants, the upper layer can also be provided with an adhesive layer with which the needle comes into contact later on.

In particular in order to be able to achieve the height of the syringe needle, i.e. its dimension transversely to its longitudinal direction (i.e. in the end effect its diameter) with the receiving device region, it is advantageous when a layer of the second label region is subjected to a deformation step, for example a hot or cold forming, in particular an stamping process. In such a layer, in particular a substrate like the carrier substrate and/or the previously mentioned upper layer (wherein the upper layer can also act as carrier substrate), and very particularly a film, a depression is preferably formed during the forming step which in the end product—i.e. in the completed label—projects from the extension surface. The depression in this case defines a desired needle receiving channel or locking channel for the syringe needle at least in regions. It therefore forms a kind of "case" or "coffin" for the syringe needle at least partially. For this purpose, the depression can be larger than or equal to the diameter of the syringe needle, but it can also be dimensioned smaller, so that further part build-up layers of the build-up layer and/or an opposite layer substantially shaped mirror-inverted equalise the remainder of the diameter. It is thus particularly preferred that a needle receiving channel is formed through the (part) build-up layers and the deformed layer(s), which is dimensioned so that the syringe needle can be adequately accommodated therein and be securely introduced.

The carrier substrate for the build-up layer can comprise a second substrate which is distinct from the actual basic substrate of the label, for example a second substrate which is affixed or laminated/attached to the basic substrate as lining. The build-up layer can then be righted in the direction of the basic substrate of the label in order to achieve a certain height between the basic substrate and the carrier substrate. Basic substrate is the term used for the substrate of the label, which substantially forms the basic label material, i.e. which defines the extension area of the label and on which the adhesive layer and/or an information print mentioned at the outset is applied for example directly or indirectly.

Preferably, the carrier substrate itself however is formed as basic substrate of the label. This means that the build-up layer is applied to this basic substrate (if required with additional layers reinforcing the basic substrate between the basic substrate and the build-up layer). Thus, both an information print in the first label region can be applied for example as well as the build-up layer in the second label region, wherein the first and the second label region are then joined together based on the basic substrate. This simplifies the manufacturing process; in particular, a separate printing (or other application of the build-up layer) on the carrier substrate and on the basic substrate can be avoided. Complicated laminating or lining processes as well as turning processes of the web of the basic substrate can also be saved. Preferably, the entire manufacture of the label is specifically without turning, i.e. without turning the basic substrate during the manufacturing process.

A further preferred embodiment of the invention consists in that at least one layer of the second label region, preferably a basic substrate, is equipped with weak portions. Here it is also true that this layer in particular comprises a substrate such as the carrier substrate and/or the previously mentioned upper layer (wherein the upper layer can also act as carrier substrate), and very particularly a film. Such a weak portion can for example serve to make it possible that the syringe needle can be introduced into the needle receiving device specifically along this weak portion. In addition, weak portions can also be provided in other regions of the label, for example in order to define a joint axis, which makes possible folding the second label region downwards from the first label region. To this end, the abovementioned prior art is referred to specifically.

Particularly preferably, the weak portions of the layer are formed as weak portions in the material, through which the syringe needle can be pressed. The layer, for this purpose, can be locally reduced in its layer thickness for example or punched along a punching line. Here, the punching can be continuous, but it can also be formed as an interrupted punching line in the manner of a perforation. Here, the perforation then comprises preferentially punched portions which are identical in length and/or identically spaced from one another, wherein these need not necessarily be realised as through-punched portions, but also as such which are not punched through. Particularly advantageous in this case is a perforation along a desired needle receiving channel of the syringe needle, which perforation is designed so that it is torn open by a maximum force of 5 N exerted on the film by the needle. A perforation can be created for example through punching, however also through laser ablation of the layer, wherein this laser ablation can also comprise the removal of only a part of the layer concerned—this applies also to any other type of the weak portion.

A particular form of such a die-cut consists in an uneven shape. For example, a wave-shaped and/or zig-zag shaped and/or crenellated die-cut form. This die-cut form preferably runs along a desired needle receiving channel of the syringe needle. Through the uneven shape of the die-cut along its entire course, a certain overlap of the punched layer over the needle receiving channel is achieved both sides of the needle receiving channel for example alternatingly, as a result of which the syringe needle can be locked simpler and more effectively.

Alternatively or additionally, layers or substrates, through which for example during the use later a needle is to be pressed, can also be partially or over the full area be formed of a material that can be easily torn such as for example paper or aluminium foil.

In principle, the build-up layer can be applied in any desired state of aggregation. It can be applied for example as powder layer, applied as film lining or deposited as vapour. It is preferred that a liquid build-up layer is applied. Liquid build-up layers are also to mean any types of at least pasty, i.e. highly viscous substances or substance mixtures, also low-viscosity substances or substance mixtures, for example with a viscosity of water. This is then a build-up layer which further hardens or is capable of hardening subsequent to the application on the carrier substrate. This therefore includes for example highly-liquid to highly viscous printing inks, varnishes, adhesives, melts and much more. The hardening takes place automatically (following suitable hardening time) or through suitable additional measures. Hardening for example takes place through solidification (in the case of melts) and/or drying and/or (for example UV-light-based) subsequent cross-linking, e.g. also subject to chemical reaction, for example in the case of two-component mixtures. The use of a liquid build-up layer offers the advantage among others that it can be applied into the carrier substrate in a simple and controlled manner and is (re)formable thereafter. The moulding of the build-up layer takes place accompanied by its hardening, so that ultimately there is a substantially solid build-up layer at the end of the moulding. However, such a solid build-up layer can nevertheless be formed elastically deformable, which is also preferred under certain preconditions for example for receiving the needle point of the syringe needle.

An advantageous configuration when using a liquid build-up layer consists in that the build-up layer comprises a form-able casting layer which is re-hardened during and/or after the moulding. By means of this, particularly high layer thicknesses of the build-up layer can be realised. For example, a melt, for example a hot melt or a similar substance mixture can be applied and moulded.

The type of the application of the build-up layer can be selected in any way per se. Thus, it can be realised through spray application, any type of coating method (doctor blade application, vapour coating, jet coating) drip application and much more. Particular advantages are obtained if the build-up layer is at least partially applied by printing: the print, in particular the screen and flexographic print in this case, is a particularly suitable application method in the label technology here. It can be used to achieve quite high layer thicknesses, especially in screen print, as they are particularly desired in the present case in order to offset the diameter of the syringe needle as far as possible with respect to height. Further preferred printing methods, with which particularly large layer thicknesses can be achieved are stencil printing and laser sintering. The respective selected printing method can be carried out both rotatorically as well as semi-rotatorically or in the flat bed. A further advantage of printing consists in that modern printing methods are also highly precise and result in reproducibly high-quality results over a long period of the production. Since printing processes are employed during the production of the label anyhow, for example for printing in the first label region, synergy effects develop during the print application of the build-up layer (or of parts of the build-up layer) for example in that a common printing unit and/or a common dryer can be used for printing both label parts. This brings with it both process-related as well as time and thus ultimately cost savings.

During the print application, overprinting can be carried out in a plurality of printing steps. Here, the individual printing steps are then preferably separated from one another in each case through a complete or partial hardening process. Through this measure, the layer thicknesses of the build-up layer in the final analysis can be selected almost as desired. However it is advantageous in terms of the technical process if the print application takes place in a single printing step. Depending on the printing method, layer thicknesses of up to 200 μm can be achieved here.

It is preferred in particular within the scope of said printing method that the printing ink used during the print application comprises for example a UV-cross linkable acrylate straight or copolymer. This material, which is used for example for realising haptically perceivable things for the visually challenged and the blind, for example also for printing warning instructions onto pharmaceutical labels, can be employed here with a particular benefit because of the particularly high layer thicknesses that can be realised.

According to a further embodiment, a printing ink or a printing varnish is applied during the print application of the build-up layer, which for example can be activated after the application. This means that the printing ink or the printing varnish only develops its final form and/or condition such as for example its adhesiveness, porosity, elasticity and much more only after the application through a suitable internal or external activation. A particularly advantageous example for such an activatable printing ink is a printing ink that can be subsequently expanded with respect to its volume, which during and/or after the application is expanded through activation for example through foaming-up because of its inherent characteristics or through exposure to radiation. By means of this, its form and layer thickness can be varied to a significantly greater degree than would be the case with non-activatable printing inks.

Alternatively or additionally to the use of a liquid build-up layer, the application of the build-up layer can comprise an application of a film. This film can then be suitably moulded after its application, for example in a hot forming step, similar to a hot adhesive layer. Alternatively, a stamping method can be employed and if applicable the film concerned can be formed jointly with the carrier substrate of the second label part. It is true in general with respect to forming methods within the scope of the present application that substrates can be formed to a greater degree during hot forming than is the case with cold forming and that they become less brittle because of the lower internal stresses. By contrast, cold forming has the advantage above all that in general terms it is a simpler process, in particular since heating can be omitted, which process can be carried out more rapidly and with less effort because of this.

As regards the overall thickness of the build-up layer it is preferred that this is around at least 200 μm, preferably around at least 300 μm, particularly preferably around at least 400 μm. Such an overall thickness of the build-up layer is aspired in order to achieve preferably a large part of the needle diameter, particularly preferably the entire needle diameter in terms of height. Syringe needles typically have diameters between 300 and 650 μm.

In principle, the build-up layer can be applied to the carrier substrate over the full area and then during the moulding, can be locally varied purely in its layer thickness. A particular attention of the invention however is placed on the part-area application of the build-up layer on the carrier substrate, in particular as a function of a desired needle receiving channel of the syringe needle. The form of the build-up layer is therefore selected so that the needle receiving channel at least in regions remains free of the build-up layer. Here it is preferred, in particular, that the build-up layer is applied to both sides along the desired needle receiving channel of the syringe needle, for example in the form of a continuous line on both sides of the needle receiving channel. In the process, the build-up layer can for example be formed as a punched film running about the desired needle receiving channel at least in regions, i.e. as a punched part for forming the needle receiving channel.

In general, a build-up layer which is formed as a function of the desired receiving channel, reflects this needle receiving channel in its fundamental course; it defines it visually as well as haptically.

In addition to the continuous form, the build-up layer can also be configured in an insular form along the desired needle receiving channel. In this case it therefore comprises a plurality of individual, discrete build-up layer regions isolated along the carrier substrate, which for example can be formed dot-shaped. Other, for example elongated, forms of the build-up layer regions along the needle receiving channel are likewise possible.

In general, the build-up layer can be applied to both sides of the desired needle receiving channel so that individual insular regions of the build-up layer are arranged offset with respect to one another on both sides of a longitudinal extension of the needle receiving channel. This produces an alternating pattern of insular regions on this side and that side of the needle receiving channel, because of which despite their offset application uneven distribution of lateral holding forces in the direction of the syringe needle can be realised.

It is preferred, furthermore, that a preferentially cushion-like point guard is applied at a location in the second label region, at which with intended use of the label for receiving the syringe needle a point of the syringe needle is embedded. The point guard becomes cushion-like in particular through its consistency, i.e. in that the syringe needle can enter it with its point and is thereafter enclosed by it. Alternatively or additionally, the point guard can also be formed as a kind of quill, in which the needle is received. The point guard, in particular a type of "pin cushion" for the syringe needle, is always suitable for receiving the syringe needle when it is positioned so that the syringe needle with the label correctly attached to the injection body, i.e. as intended, when being introduced into the needle receiving device, contacts or enters the point guard with its point.

Here it is particularly preferred that the second label region with the cushion-like point guard is formed in such a manner and arranged with respect to the first label region so that upon the intended attachment of the label to the syringe body and upon an intended bending over of the syringe needle upon reception of the syringe needle in the receiving device region the point is introduced into the point guard, preferentially pricked into in a positively guided manner. This can be realised in particular in that when bending over the syringe needle two different radii play a role: the second label region, when bending over the syringe needle is supported on a side of the syringe needle or is even still slightly spaced from it. If the needle is now bent, an internal radius of the bend of the syringe needle which is smaller than the outer radius of the bend of the syringe needle is obtained and thus of necessity also the bend of the label. With its outer end arranged on the point of the syringe needle, the second label region is therefore slightly moved in the direction of the syringe body during the bending along the syringe needle. Because of this, the outer end including the point guard is also displaced nearer in the direction of the point of the syringe needle, and receives the latter within itself.

Preferentially, the cushion-like point guard comprises an elastically deformable and/or plastic layer, which can be deformed and/or moved, i.e. displaced by the syringe needle from a starting form or starting position into a transition form or transition position at least in regions and at least partially automatically moves back in the direction of the starting position following an insertion or engaging of the syringe needle. Because of this, the point guard firmly encloses the point of the syringe needle, thereby embedding it. The syringe needle thus enters the point guard with a preferably low force and is then subjected to a preferably higher force, which holds it in the point guard. Particularly preferred suitable materials for forming the point guard are for example PU-resins, acrylates, silicones, PU/acrylate copolymers, foams etc. The point guard can be preferably designed so that the needle can be inserted into the point guard but not completely pierced. This can also be realised in that the point guard consists of different materials in regions.

Particularly preferably, the cushion-like point guard is designed larger in its areal and/or height dimensioning with respect to the carrier substrate than other regions of the build-up layer, in particular than other insular regions of the build-up layer. Thus it protrudes further from the surface of the carrier substrate so that it can fulfil a better embedding function than the other regions of the build-up layer.

As mentioned above, the moulding, i.e. shaping of the build-up layer can be effected on the one hand, through the specific application of the build-up layer and/or through moulding the build-up layer already applied once. An advantageous special case of the latter procedure consists in that the moulding of the build-up layer into the receiving device region takes place by removing regions of the build-up layer. Such a material removal in the regions of the build-up layer thus serves for the subsequent moulding; it can be effected for example through punching and weeding. Alternatively to this, pre-punched shaped parts can also be produced and then affixed. It is particularly preferred that the removing is effected with the help of laser reworking. Removal with the help of laser beams, i.e. an ablation, can be configured highly flexibly, can be easily defined by programming the laser and integrated without problems in line in a label manufacturing process. Only little waste is incurred in the process in the form of burnt-off material, which can be specifically removed through extraction.

Between the first label region and the second label region, a transition region is preferably arranged, in which the second label region can be folded away from the first label region preferably in a defined position. Such a transition region can for example be configured significantly less wide than the other two label regions and interconnects the two regions. As part of this it is advantageous if the build-up layer at least in regions beyond the second label region, is arranged in a transition region in the direction of the first label region. Excess material of the build-up layer in this transition region can be co-removed when punching the final shape of the label. The extension of the build-up layer into the transition region can for example serve in order to reinforce the transition region in terms of thickness and material and thereby (if required), supported by a local weakening of the build-up layer in the transition region achieve a defined bending location for folding away the second label region. It is therefore particularly preferred that the build-up layer in the region of the transition region is locally weakened, preferably so that a local weakening resulting from this is formed in a direction which deviates from the longitudinal direction of the label from the first label region in the direction of the second label region. Such possible weakening patterns which can be simply produced through material recesses and/or material stamping in the build-up layer can for example be configured on the model of the European Patent Application EP 2 302 610 A2. In addition, the build-up layer can also be locally reinforced in other part regions of the transition region, for example directly next to the local weakening in order to increase the different bending radii of injection needle and label region and thus as explained above a penetration depth of the needle point into a point guard.

With respect to the first label region, this is preferably printed, particularly preferably at least with one inscription print, i.e. with signs, characters, figures or symbols indicating the content of the and certain instructions regarding the content of the syringe body. The first label region thus serves as marking region of the label.

Particularly preferably, the first label region is formed transparently at least in regions and the printing comprises an inscription print, which at least in regions is backed by a covering, preferentially a covering white, printed opaque layer. Such opaque layers can for example be produced through screen printing. Alternatively to the opaque printing of a transparent first label region, an opaque first label region can also be used. The second label region can also be opaque, for example also printed in a covering opaque manner, wherein other colours can also be used here, for example a signal colour such as red for the better detectability of the needle receiving device. The material of the build-up layer can also be preferably held in such a signal colour entirely or partially.

In principle, the printing of the first label region can be carried out on both of its flat sides, while it is preferably carried out on the first flat side, particularly preferably by reverse printing on transparent substrate, so that a user is able to correctly read the print from the other flat side. When printing the first flat side of the first label region, the build-up of the needle receiving device can take place on the same flat side so that no turning in the production is necessary. Through the reverse print, the print is automatically protected towards the user after the application of the label to the syringe body through the substrate of the label above the print. Alternatively, a direct print can also be carried out, i.e. a print in an orientation in which the print is legible or understandable from the printing side.

In order to equip the label to be self-adhesive, furnishing the first flat side of the first label region at least in regions with an adhesive following the printing of the first flat side of the first substrate part is carried out according to a first variant.

This can take place both through the print-application of adhesive as well as through lining with an adhesive layer.

According to a second variant, the first label region and the second label region are formed of a continuous substrate material coated with an adhesive. As substrate material, a pre-coated self-adhesive material is thus used, which has the advantage that the adhesive characteristics can already be optimally selected in advance and standard materials can be employed.

In general, there are the three possibilities of using a substrate material which is not coated with adhesive, a substrate material that is partly coated (partially coated) with adhesive or a substrate material that is coated with adhesive over the full area as base material. In the case of fully coated substrate materials and if applicable also with the coated substrate materials, an adhesive effect of the adhesive is preferably reduced at least in regions at least in the second label region. Such a so-called "adhesive killer", i.e. the printing of a varnish layer or alternatively a covering film lining on the adhesive helps to reduce and preferably completely cancel the adhesive effect of the adhesive in the locations in which it is undesirable. This is desired in particular in the regions of the label which can come in contact with the environment, i.e. with users or the air in order to prevent contaminating the label, for example through dust.

As a rule, labels are provided on carrier webs, usually of siliconised paper or siliconised film. Within the scope of the invention it is preferred that the label is provided on a carrier web which is recessed at least in regions in the region of the second label region. This results in a certain thickness reduction in the region of the second label region and in addition, the abovementioned adhesive killer can be applied to the first flat side of the label exactly there instead of the carrier web, so that the separating effect of the carrier web does not apply anyway.

Furthermore it is preferred that the label is provided on a carrier web which at least in regions in the region of the first label region is equipped with a spacing layer for the height compensation of the height of the needle receiving device. To this end, the carrier web is preferably provided with the spacing layer on its flat side facing away from the first label region, which can for example be printed, otherwise be applied in liquid form, if required, even be foamed on as well. Alternatively, a spacing layer can be laminated onto the carrier web in this region. Through the spacing layer, the first label region plus the carrier web and exactly that spacing layer, preferably has substantially the same thickness as the second label region with its needle receiving device. Because of this, the winding up on a roll is substantially facilitated and an entangling of the needle receiving regions in the wound-up state is avoided.

With the previous manufacturing method for labels of the type mentioned at the outset, the pick-and-place method always took place on a label web with only one copy: because of this, the needle guard device could always be affixed from the same side. This means that previously either a semifinished product of the label was being produced in a plurality of copies which were then separated from one another prior to affixing the needle guard device or that a label web with only one copy was produced in the first place, to which the needle guard devices were then affixed at the end of the manufacturing process. Since the affixing of separate parts with the method according to the invention becomes obsolete, however, in principle, it is preferred within the scope of the invention that the label is produced in a plurality of copies arranged next to one another in a web course direction, which copies are preferably rolled up from one another after a completion of the production of the label, particularly preferably separated and individually rolled up. This means that at least the application and moulding of the build-up layer is carried out on a multiple-copy label web which is substantially more effective and space and cost saving for the production.

Preferably, the label is entirely produced in a roll-to-roll process. This means that at least the basic substrate of the label, preferably all supplied substrates, are supplied in webform from the roll and that the end product, i.e. the completed label, is likewise wound up on a roll again. Here, the web advance takes place preferably continuously, so that high production speeds can be achieved. In this respect it is preferred, furthermore, that all modules or stations employed in the process also operate in a continuous process, i.e. in the case of printing couples and punches that these are formed at least semi-rotatorically.

Preferentially, the label is punched only after the application and the moulding of the build-up layer in the region of the second label region so that the shape of the second label region is obtained. This means that during the application and moulding process an even larger carrier substrate is present than with the end product. Because of this, these two processes can be handled in a simpler and more controlled manner since the sturdiness of the web is increased by this.

A label, in which the second label region comprises at least one basic substrate as carrier substrate and an upper layer on a flat side of the basic substrate as well as a weakened portion in the basic substrate and/or the upper layer has proved to be particularly advantageously produced and highly functional according to the invention, wherein the basic substrate and/or the upper layer is three dimensionally formed subject to forming a needle receiving channel and wherein on the layer comprising the weakened portion a build-up compound is arranged in both sides of the weakened portion. The build-up compound, together with the upper layer, in this case jointly forms the build-up layer. The build-up compound is thus a part build-up layer. It can be arranged between the basic substrate and the upper layer and/or on the flat side of the basic substrate facing away from the upper layer. Here, the build-up compound preferably extends in each case at least partially substantially parallel to the fundamental course of the weakened portion. Such a label, the construction of which is also described in more detail by means of the Figures has the advantage that it can be produced particularly easily namely in particular without turning the basic substrate, since all process steps of the manufacture can be carried out from an upper flat side of the basic substrate without exception.

Figure 16A:
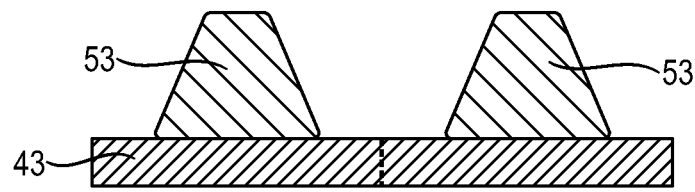
Figure 16B:
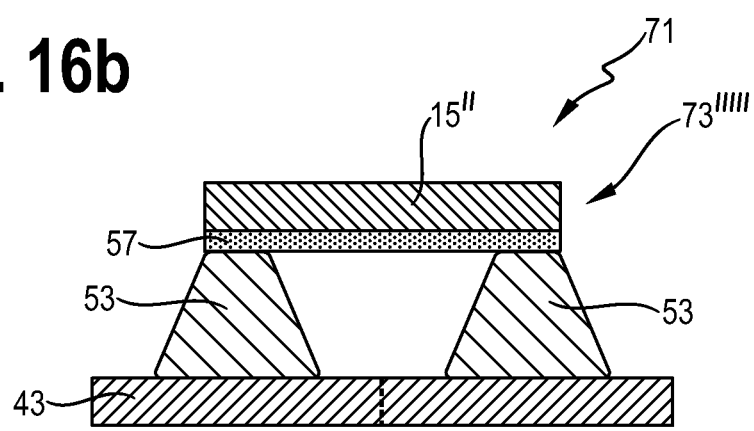
Figure 16C:
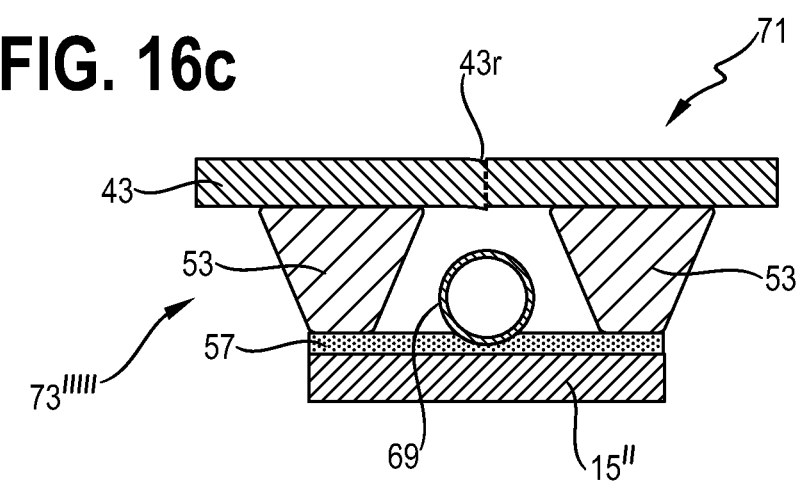
Figure 17A:
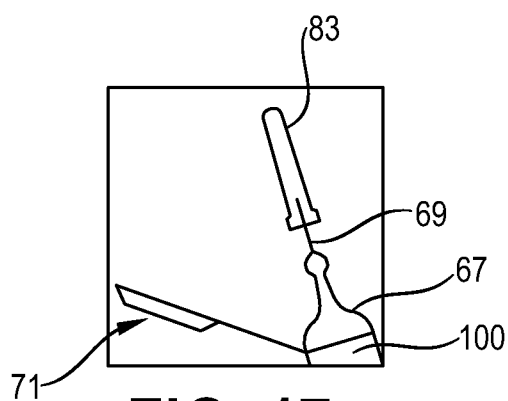
Figure 17B:
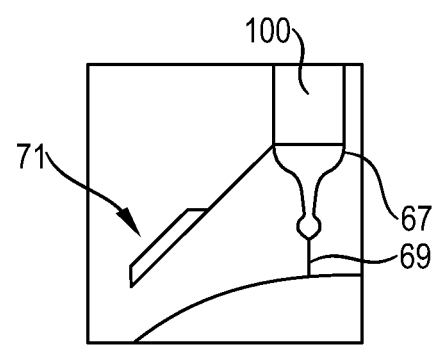
Figure 17C:
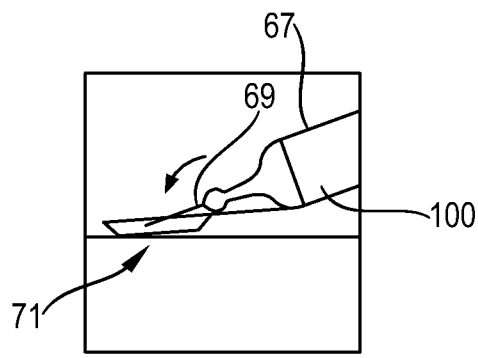
Figure 17D:
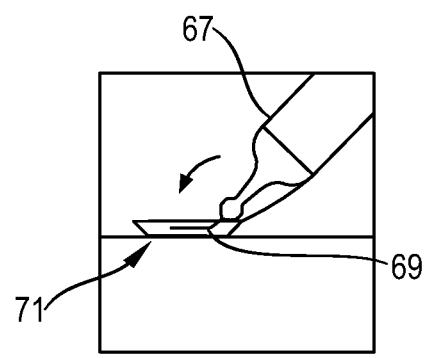

In the following, the invention is once more explained in more detail by means of exemplary embodiments making reference to the attached Figures. Here, same components are provided with identical reference characters in the various Figures. Layers and components are not necessarily reproduced to scale. It shows:

FIG. 1 a schematic function representation of an exemplary embodiment of a machine according to the invention, FIGS. 2a to 2c, three views of a first process product of a preferred embodiment of a method according to the invention, wherein FIG. 2a shows a sectional representation along a section line A-A and FIG. 2c a sectional representation along a section line C-C in the perspective representation in 2b, FIGS. 3a to 3c, three views of a second process product of the same embodiment of the method according to the invention with the same representation views as in the FIGS. 2a to 2c, FIGS. 4a to 4c, three views of third process product of the same embodiment of the method according to the invention with the same representation views as in the FIGS. 2a to 2c, FIGS. 5a to 5c, three views of fourth process product of the same embodiment of the method according to the invention with the same representation views as in the FIGS. 2a to 2c, FIGS. 6a to 6c, three views of fifth process product of the same embodiment of the method according to the invention with the same representation views as in the FIGS. 2a to 2c, FIGS. 7a to 7c, three views of sixth process product of the same embodiment of the method according to the invention with the same representation views as in the FIGS. 2a to 2c, FIGS. 8a to 8c, three views of seventh process product of the same embodiment of the method according to the invention with the same representation views as in the FIGS. 2a to 2c, FIGS. 9a to 9c, three views of eight process product of the same embodiment of the method according to the invention with the same representation views as in the FIGS. 2a to 2c, FIG. 10 shows a perspective view from the front of an embodiment of a label according to the invention, produced with the method shown by means of the FIGS. 1 to 9c, FIG. 11 shows a lateral perspective view of the same label as in FIG. 10, FIGS. 12a and 12b show a perspective view and a view from the top of a region of a second embodiment of a label according to the invention, FIGS. 13a and 13b show a perspective view and a view from the top of a region of a third embodiment of a label according to the invention, FIGS. 14a and 14b show two lateral views of a region of a fourth embodiment of a label according to the invention, FIGS. 15a and 15b show a perspective view and a lateral view of a region of a fifth embodiment of a label according to the invention, FIGS. 16a to 16c, three sectional representations through a region of a semi-finished product (FIG. 16a) and a finished label (FIGS. 16b and c) according to a sixth embodiment of the invention, FIGS. 17a to 17d, schematic representations of a process of the use of an embodiment of a label according to the invention upon application of a syringe.

FIG. 1 shows an embodiment of a machine 1 according to the invention for producing an embodiment of a label 100 according to the invention. Here, reference is simultaneously made to the FIGS. 2a to 10, for along the web course through the machine from left to right reference is made to the statuses of the respective process product through Roman numerals. The Roman numeral II thus refers to the FIGS. 2a to 2c, the Roman numeral III to the FIGS. 3a to 3c and continues in this way. The Roman numeral X refers to the FIG. 10.

From a first roll 2, a self-adhesively coated transparent substrate material 3 is supplied which comprises a 36 μm thick PET-film. The substrate material 3 is schematically shown in different representations in the FIGS. 2a to 2c. In all FIGS. 2a to 9c, all figures marked with "b" are perspective representations on a portion of the respective material web shown along the web course in the machine 1, the figures marked with "a" are sectional representations transversely to this web course along the section lines A-A and the figures marked with "c" are sectional representations parallel to the web course along the section lines C-C.

The substrate material 3 comprises a basic substrate 43 with an extension area E and a first flat side $F_1$ and a second flat side $F_2$. On its second flat side $F_2$, it is coated with a pressure-sensitive adhesive 41 over the full area. On the side of the adhesive 41 facing away from the basic substrate 43, a carrier web 39 is arranged, which covers the adhesive 41 over the full area.

The substrate material 3 in the machine 1 (see FIG. 1) is supplied to a punching unit 5. This punching unit 5 punches weakened portions 45 (see FIGS. 3a to 3c) in the form of wave-shaped die-cuts 45 through the basic substrate 43. This results in a punched substrate material 3'. Here, the carrier web 39 is preferably not punched in the process.

A first rotary flexographic printing unit 7 of the machine 1 comprises a printing roller 7b, which is directed in the direction of the first flat side $F_1$ and a counter-roller 7a, which is directed in the opposite direction, i.e. in the direction of the second flat side $F_2$. The punched substrate 3' is printed in this first printing unit 7, just as in a second flexoprinting unit 9. The second flexoprinting unit 9 comprises a printing roller 9b and a counter-roller 9a, which are orientated and arranged analogously to the rollers 7a, 7b of the first printing unit 7. The printed substrate material 3", which is shown in the FIGS. 4a to 4c, results from these two printing steps:

In the first printing unit 7, an information print 55 was printed on in a first label region 51. This information print 55 has an opaque white layer and a print with characters and symbols applied against the viewing direction onto the first flat side $F_1$ on the opaque white layer. For the sake of simplicity, the information print 55 was represented as a print layer, printed in a printing operation. However, it can also (especially when printing with a plurality of layers positioned on top of one another, this is not necessary) be produced in a plurality of separate printing operations. The information print 55 in the first label region 51 serves for the marking function of the label to be produced: it describes the syringe body to be labelled and especially its content in more detail; the printed characters and symbols thus are in particular information regarding the content and size of the syringe.

In a second label region 47, which is joined to the first label region 51 through a transition region 49, a first part build-up layer 53 as part of a build-up layer 73 was printed in the second printing unit 9. The first part build-up layer 53 comprises a build-up compound 53 of for example a UV-cross linked acrylate copolymer, which in each case is applied and moulded U-shaped about the die-cuts 45. The U-shapes in this case are orientated so that they are open in the direction of the first label regions 51 and closed in the opposite direction. The two legs of the U-shapes are each located parallel to the fundamental course of the die-cuts 45, which enclose them. The moulding of the build-up compound 53 in this case is effected through a selective printing of the substrate material 43, which here serves as carrier substrate 43 for the build-up compound and for the build-up layer 73 as a whole.

Figure 5A:
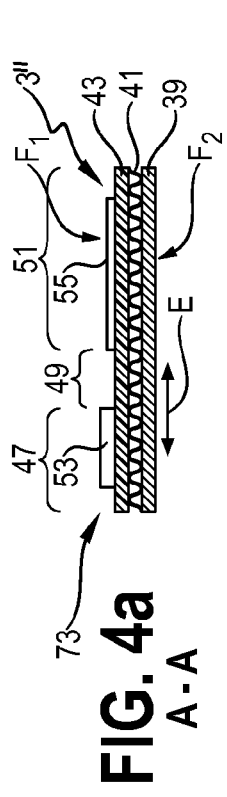
Figure 5B:
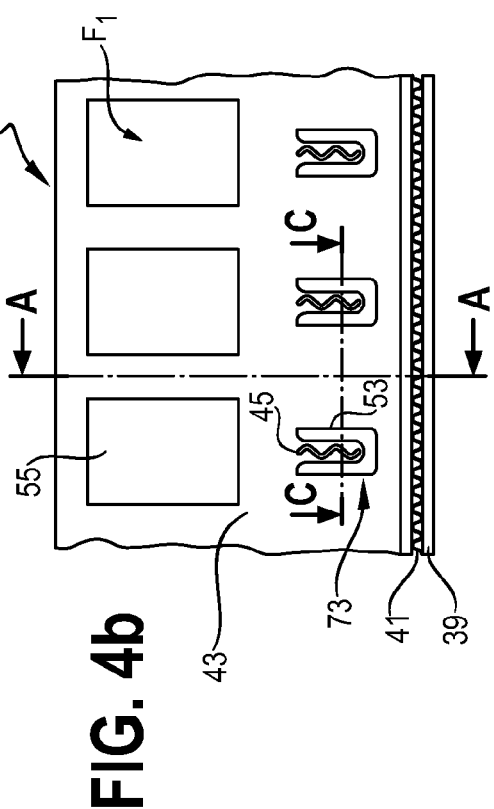
Figure 5C:
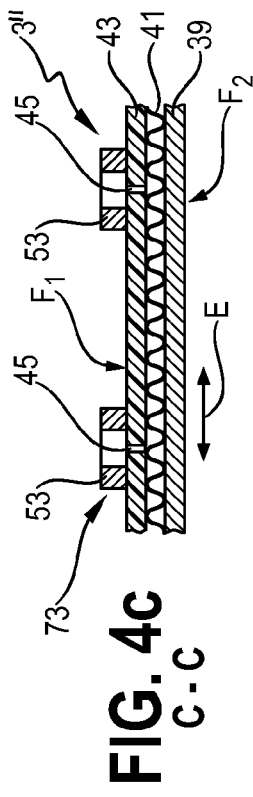
Figure 6A:
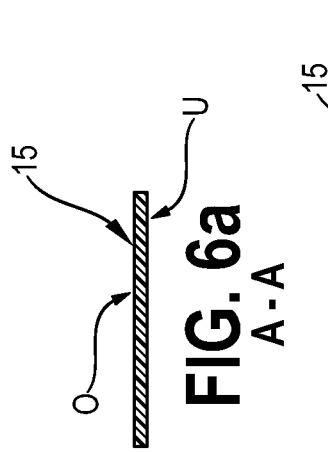
Figure 6B:
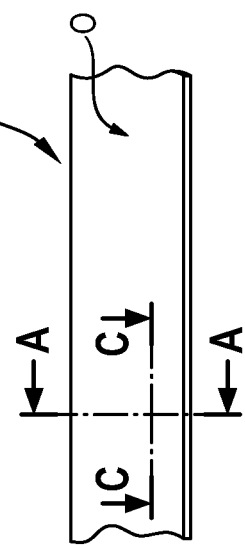
Figure 6C:
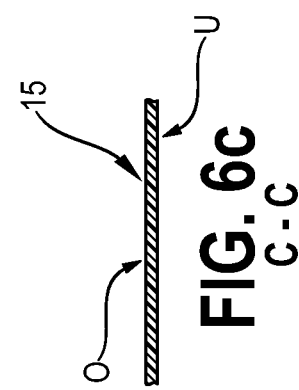
Figure 7A:
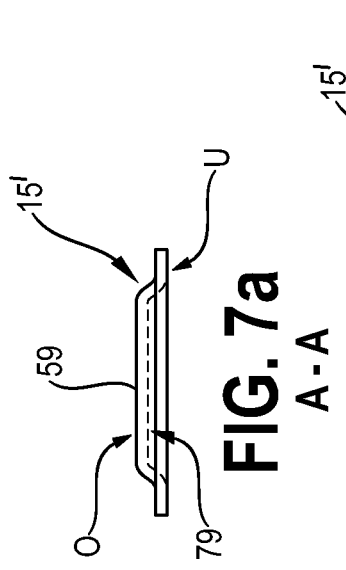
Figure 7B:
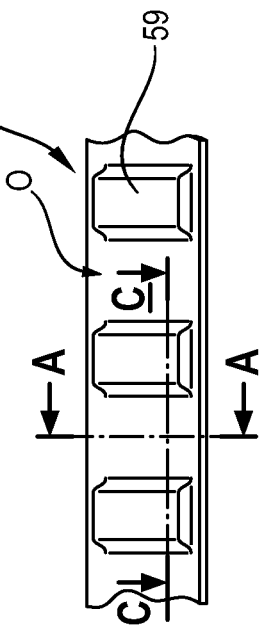
Figure 7C:
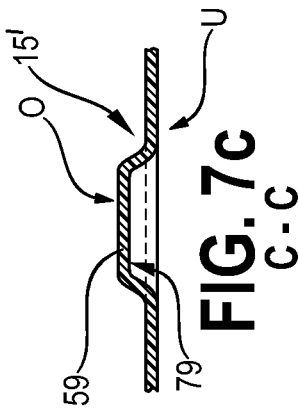

In a laminating printing unit 11 (see FIG. 1) with a printing roller 11b and a counter-roller 11a in the same orientation as the two printing units 7 and 9, the printed substrate material 3" is coated over part of the area with a lining varnish 57. FIGS. 5a to 5c show the substrate material 3''' coated with the lining varnish 57. The lining varnish 57 extends over and beyond the build-up compound 53; if appropriate, it can also be omitted in the region of the die-cut 45 so as not to close the die-cut 45 again. Both the build-up compound 53 as well as the lining varnish 57 now form the build-up layer 73 as part build-up layers 53, 57.

The lining varnish 57 serves to apply an upper layer 15 in the form of an upper film 15 in a lining unit 13 with an upper lining roller 13b and an opposing lining roller 13a, analogously to the previously mentioned printing units 7, 9, 11. The preparation of this upper film 15 is explained by means of the FIGS. 1, 6a to 6c and 7a to 7c:

From a roll, the upper film 15, which comprises a 125 µm thick PP-film is provided. The upper film 15 with an upper side O and a lower side U is shown in the FIGS. 6a to 6c. In a stamping unit 17, with a concavely orientated stamping mould 17b and a convexly orientated counter-stamping mould 17a, the upper film 15 is hot-stamped. The result of this stamping is a case-like depression 79 shown in FIGS. 7a to 7c on the lower side U of the upper film 15 and a curvature on the upper side O of the upper film. The position and size of the depression 79 corresponds to those of the build-up compound 53, as is evident from the following Figures.

By way of a deflection roller 19 (see FIG. 1) and the lining unit 13, the coated substrate material 3''' is lined with the upper film 15 so stamped. Here and in the following steps, the stamped region is preferentially recessed in order to obtain the stamping. This results in the lined substrate material 3'''' shown in FIGS. 8a to 8c. Through a register-accurate application of the upper film 15 in a manner that the case-like depression encloses exactly the build-up compound 53, the build-up layer 73 now comprises the build-up compound 53, the lining varnish 57 and the upper film 15, each in the region of the build-up compound 53. This build-up layer 73 jointly with the carrier substrate 43 forms the needle receiving device later on.

In the following, the lined substrate material 3'''' is treated further at the bottom: a slitting unit 21 to this end slits the carrier web 39 in web running direction below the transition region 49, nearer to the first label region 51 than to the second label region 47. By way of a weeding unit 23 with a top-side roller 23b and a bottom-side deflecting roller 23b, the part of the carrier web 39, which was located on the bottom side (i.e. on the second flat side $F_2$) in the second label region 47 and a part region of the transition region 49, is wound onto a roll 25. The rest of the carrier web 39 remains on the lined substrate material 3''''. In a fourth printing unit 27 with a bottom-side printing roller 27a and a top-side counter-roller 27b, the lined substrate material 3'''' is now coated on the bottom side with a varnished layer 61 (as adhesive killer). This is performed where the adhesive 41 is exposed because of the partial removal of the carrier web, so that the adhesive effect of the adhesive 41 is preferably largely cancelled in this region.

In a fifth printing unit 29 with a printing roller 29a and a counter-roller 29, a spacing layer 63 is printed likewise at the bottom over the full area onto the remaining region of the carrier web. During the subsequent winding up of the finished label webs, this serves for the height compensation between the first label region 51 and the second label region 47, since the latter obviously has become significantly thicker through the build-up layer 73 than the former.

These last described slitting and printing steps result in the semi-finished product 3''''', which are shown in FIGS. 9a to 9c. Here it is evident especially in FIG. 9a that the carrier web 39 is now only present on the right side, while the adhesive 41 is covered on the left side through the varnish layer 61 over the full area. Below the remaining carrier web 39, the spacing layer 63 is applied. The layer 63 can also be applied discontinuously or over part of the area.

Finally, the semi-finished product 3''''' is customised into the finished product 100. To this end, the contours of the label are punched out by means of a punch 31. At a weeding station 33 with an upper roller 33b and a lower roller 33a the waste weed is separated from the finished label and wound onto a waste roll 35, while the web with the finished labels is wound onto a label roll 37.

The end product of this method is shown in the FIGS. 10 and 11. Here it is noticeable that the resulting label 100 comprises three substantially quadrangular regions (from the top down in FIG. 10): The first label region 51, whose contour corresponds to the outer contour of the information print 55, is joined to the carrier web 39 by the adhesive 41. The second label region 47 comprises the needle receiving device 71, which is formed from the build-up layer and the punched carrier substrate 43. The second label region 47 is smaller dimensioned than the first label region 51 both in longitudinal as well as in transverse direction of the web course. The two label regions 51, 47 are joined together through the transition region 49, which approximately has half the length (transversely to the web direction) of the second label region 47 and which is embodied significantly narrower (in web direction) than the two label regions 51, 47.

At its lower side in FIG. 10, i.e. in the region which closes off the die-cut 45 facing away from the first label region 51, the build-up compound 53 within the needle receiving device 71, is simultaneously embodied as a point guard 77. A point of a syringe needle can enter a short way into the region of the point guard and because of this be held therein firmly embedded.

The label 100 can now be wound and glued onto a syringe body with the help of the adhesive 41 in the first label region 51. Because of this, it is orientated in the second label region 47 with its second flat side $F_2$ in the direction of the syringe needle of the syringe body and when applied as intended is positioned so that the second label region 47 is arranged substantially parallel to the syringe needle along the continued course of the syringe body. Because of this, the second label region faces with the second flat side $F_2$ and thus with the die-cut 45 in the direction of the syringe needle. By contrast, the information print 55 on the first flat side $F_1$ faces away from the syringe body, so that it is legible to a user. Following the administering of the injection to a patient, the syringe needle can be introduced through the die-cut 45 between the carrier substrate 43 and the upper film 15 by pressing onto the second flat side $F_2$ in the second label region 47. By forming the upper film away from the syringe needle and through the build-up compound 53, a needle receiving channel 65 is formed in which the syringe needle finds adequate space and in which it remains securely accommodated. By pricking the point of the syringe needle into the point guard 77 and through the holding effect of the die-cut 45 because of its wave shape, the syringe needle firmly remains in this needle receiving channel 65.

The machine, which was described by means of the FIG. 1 and indirectly by means of the FIGS. 2a to 11, comprises, according to the invention, an application and moulding device 200. It establishes the needle receiving device 71 by applying the build-up layer 73 on the carrier substrate 43 of the second label region 47 and by moulding the build-up layer 73 on the carrier substrate 43 into a receiving device region wholly or partly forming the needle receiving device 71. To this end, it comprises in the present case the second printing unit 9, the lining printing unit 11, the stamping unit 17 and the lining unit 13.

FIGS. 12a and 12b show a part region of a second label region of a second embodiment of a label according to the invention. Here, a build-up compound 53' is again applied to a carrier substrate 43 and a flat upper film 15' applied as lining thereon. The build-up compound 53' and the upper film 15' as part build-up layers form a build-up layer 73' of a needle receiving device 71. The upper film 15' is weakened through a weakened portion 45, here a linear punched perforation 45'. A needle receiving channel 65 extends below the punched perforation 45', between two lines of the build-up compound 53' which are separated from each other and run in parallel. A syringe needle can be introduced into this needle receiving channel 65 by pressing through the punched perforation 45' analogously to the previously described label.

FIGS. 13a and 13b show a part region of a second label region of a third embodiment of a label according to the invention. Here, the build-up layer 73" consists of a build-up compound 53" applied in an insular, namely dot-shaped form onto a carrier substrate 43, onto which a second build-up compound 75 is then applied in a cantilever-projecting manner. This produces a mushroom shape of the build-up layer 73" in cross section. FIG. 13b shows that the individual insular part regions of the build-up layer 73" are attached offset with respect to each other along a needle receiving channel 65, the course of which is explained through a syringe needle 69 with a point 81. It also becomes clear that the second build-up compound 75 following the embedding of the needle in the needle receiving channel 65, projects cantilever-like at the top and is again securely held because of this.

FIGS. 14a and 14b show two lateral views each of the same part region of a second label region of a fourth embodiment of a label according to the invention. On a carrier substrate 43, two build-up layers 53''', 77' are applied here in the direction of a syringe needle (when the label is applied to the syringe body). While the smaller dimensioned first build-up layer 53 runs on both sides of a needle receiving channel analogously to FIGS. 13a and 13b, the second build-up layer 77' is dimensioned larger in its layer thickness. It forms a cushion-like point guard 77', into which the point 81 of the syringe needle 69 is pricked. To this end, as is evident by means of FIG. 14b, the syringe needle 69 is bent about an inner radius $r_1$. Through this bending, the second label region of the label is also inclined in the bent region by a larger radius $r_2$, so that its end region equipped with the point guard 77' is forcibly displaced in the direction of the point 81 of the syringe needle 69. Because of this, the point 81 of the syringe needle 69 automatically pricks the point guard 77' and is thus held. Because of this, users can no longer injure themselves on the point 81.

FIGS. 15a and 15b each show a part of a second label region of a fifth embodiment of a label according to the invention. Here, FIG. 15a shows a perspective view of the needle receiving device 71 from the top prior to a use, i.e. before inserting a syringe needle, and FIG. 15b a lateral view (analogously to the representation of the fourth embodiment in FIG. 14b) of the needle receiving device 71 with introduced and bent injection needle 69.

To produce the needle receiving device 71 according to the FIGS. 15a and 15b, a build-up compound 53 was again printed onto a carrier substrate 43 as first part layer of the build-up layer 73'''', wherein in principle the same build-up compound 53 as with the exemplary embodiment according to the FIGS. 1 to 10 can be used. Here, too, the build-up compound 53 is applied to the carrier substrate 43 subject to the forming of a needle receiving channel 65 substantially as a U-shaped wall 53u, wherein the U-shape is orientated so that it is open in the direction of the first label region (not shown in the FIGS. 15a and 15b). In an end region of the second label region facing away from the first label region, i.e. in the region of the U-web, an upper layer 15 in the form of an upper film 15 is applied onto this U-shaped wall 53u as lining by means of a lining varnish (not shown in the FIGS. 15a and 15b), which spans the cavity between the U-leg in this end region so that altogether a kind of point guard in the form of a quill is formed for the syringe needle 69.

As is shown by comparing the FIGS. 14b and 15b, the mode of operation of this fifth embodiment of the needle receiving device 71 is similar to that of the fourth embodiment. On bending a syringe needle 69 positioned in the region of the needle receiving device 71, the end region of the needle receiving device 71 forming the quill is moved in the direction of the point 81 of the syringe needle 69 through the bending of the second label region in the bent region by a radius which is larger than the radius of the bent syringe needle 69 itself. Considered the other way around, the syringe needle 69 is thus forcibly introduced into the point guard with its point 81. In order to support this effect, webs 53s consisting of the build-up compound 53 were applied to the carrier substrate 43 to a plurality of locations (here, specifically two locations) transversely to the longitudinal direction of the second label region. As is evident by means of FIG. 15b, the difference between the bending radii of the syringe needle 69 and of the carrier substrate 43 is increased through this, that upon bending the difference in distance between the point 81 of the syringe needle 69 and the quill is increased and the point 81 dips deeper into the quill.

A sixth embodiment of a label according to the invention is described by means of the FIGS. 16a to 16c. Only one cross section perpendicularly to the needle receiving channel 65 through the needle receiving device 71 (or a pre-stage of this needle receiving device 71 during the production) is shown here in each case. FIG. 16a in this case shows the product in a production stage in which, analogously to the production step in FIG. 4c, a build-up compound 53, for example in a U-shape or even closed all round, approximately rectangular in shape, is printed as first part layer of the build-up layer 73"" onto a carrier substrate 43 along the needle receiving channel 65. The carrier substrate 43 in this case is preferably a very thin aluminium foil, paper or a similar material, which can easily tear by itself in the region of the needle receiving channel 65 (in the area marked with interrupted line in the FIGS. 16a and 16b), so that a syringe needle can be pressed through here. Alternatively, as already explained above by means of the other exemplary embodiments, a partial weakened portion can be introduced in the carrier substrate 43.

The height of the build-up compound 53 in this case is again selected so that it is greater than the outer diameter of a needle to be received. An upper layer 15" for example in the form of an upper film 15" is then applied to this build-up compound 53 by means of a lining varnish 57 (or of another adhesive), which spans the needle receiving channel 65 preferentially over the full area. Here, the upper layer 15 is provided on the side facing the needle receiving channel 65 with the lining varnish 57 or adhesive over the full area. For example, the upper layer 15" can consist of a self-adhesive film. FIG. 16b shows a cross section through a needle receiving device 71 created in this way with a closed needle receiving channel 65 in the second label region.

FIG. 16c shows this needle receiving device 71 following the reception of a syringe needle 69. To this end, a needle while pressed into the needle receiving channel 65 from the top through the carrier substrate 43 (as is still explained in the following by means of the FIGS. 17a to 17d), wherein the carrier substrate 43 is torn open at a tearing point 43r along the needle. In the process, the syringe needle 69 is pressed onto the lining varnish 57 or the adhesive layer and held in the needle receiving channel 65 by the latter. Preferentially, a lining varnish 57 or adhesive is selected, which in the interior of the needle receiving channel 65 remains adhesive for a long time, i.e. does not harden with the carrier substrate 43 not torn.

FIGS. 17a to 17d finally show schematic representations of a process of the use of an embodiment of a label according to the invention upon application of a syringe.

A syringe body 67 according to the invention, i.e. equipped with a label 100 according to the invention, with a syringe needle 69 is presented. A syringe cap 83 is removed from the syringe needle 69 in a first step (FIG. 15*a*), while the second label region of the label 100 is folded away from the syringe needle by folding over in the transition region of the label 100. In this state (see FIG. 15*b*) the injection is administered to a patient. Thereafter (see FIG. 15*c*) the syringe needle 69 is introduced into the needle receiving device 71 of the label 100 and (see FIG. 15*d*) bent.

When carrying out these steps shown in FIGS. 15*a* to 15*d*, the schematically shown label 100 from FIGS. 10 and 11 was used here. This explains why the needle receiving device 71 faces away from the syringe needle 69.

It is pointed out once more in concluding that the components of the label or of the syringe body described in detail beforehand are merely exemplary embodiments which can be modified by the person skilled in the art in various ways without leaving the scope of the invention. In particular, the features of the embodiments specifically described above can be combined for forming other variants and the label can also be enriched with components from the prior art stated at the outset. For example, the inner side of the upper layer 15 according to the exemplary embodiment according to the FIGS. 1 to 10 can also be provided with an adhesive, for example by injecting an adhesive in the depression 79. Furthermore, the use of the indefinite article "a" does not exclude that the features concerned cannot be present in multiples as well. In addition, "units" and "modules" can also consist of one or a plurality of components which can also be arranged spatially distributed.

The invention claimed is:

1. A method for producing a label for a syringe body, wherein the label comprises a first flat side and a second flat side, said method comprising:
   providing a first label region which is configured to be wrapped about the syringe body,
   providing a second label region, which is joined to the first label region and on at least one of a first flat side and a second flat side of said second label region forming a needle receiving device configured to receive a syringe needle attached to the syringe body, and
   wherein said needle receiving device is formed by applying a build-up layer onto a carrier substrate of the second label region and molding of the build-up layer onto the carrier substrate, wherein the molding includes applying an uncured material onto the carrier substrate and curing the uncured material.

2. The method according to claim 1, wherein applying the build-up layer includes applying a plurality of part build-up layers of the uncured material;
   wherein a first part build-up layer is positioned nearer the carrier substrate than a second part build-up layer; and
   wherein the second build-up layer comprises a film-like layer.

3. The method according to claim 1, wherein the second label region includes a depression that defines a needle receiving channel for the syringe needle.

4. The method according to claim 1, wherein the carrier substrate provides a basic substrate of the label.

5. The method according to claim 1, wherein a layer of the second label region includes weakened portions.

6. The method according to claim 1, wherein the buildup layer is a liquid build-up layer.

7. The method according to claim 6, wherein the applying of the build-up layer includes printing of the build-up layer.

8. The method according to claim 1, wherein the build-up layer provides a needle receiving channel of the syringe needle.

9. The method according to claim 8, wherein the build-up layer is applied along the needle receiving channel.

10. The method according to claim 1, further comprising applying a cushion-like point guard to the second label region.

11. The method according to claim 10, wherein the second label region, with the cushion-like point guard, is formed in such a manner and arranged with respect to the first label region such that when the label is positioned on the syringe body and upon unintended bending of the syringe needle upon reception of the syringe needle in the receiving device region, a needle point of the syringe needle is positively introduced into the point guard.

* * * * *